United States Patent [19]

Sawyer

[11] Patent Number: 5,179,569
[45] Date of Patent: Jan. 12, 1993

[54] SPREAD SPECTRUM RADIO COMMUNICATION SYSTEM

[75] Inventor: Jonathan Sawyer, Golden, Colo.

[73] Assignee: Clinicom, Incorporated, Boulder, Colo.

[21] Appl. No.: 652,976

[22] Filed: Feb. 8, 1991

Related U.S. Application Data

[60] Continuation-in-part of Ser. No. 343,602, Apr. 24, 1989, abandoned, which is a division of Ser. No. 78,195, Jul. 24, 1987, Pat. No. 4,835,372, which is a continuation-in-part of Ser. No. 862,278, May 12, 1986, abandoned, which is a continuation-in-part of Ser. No. 757,277, Jul. 19, 1985, abandoned.

[51] Int. Cl.$^5$ ............................................. H04L 27/30
[52] U.S. Cl. ......................................... 375/1; 380/34; 340/573; 340/600; 340/870.03; 340/870.11; 340/870.18; 340/870.28
[58] Field of Search ................ 375/1; 380/34; 342/37, 342/45, 50; 340/505, 539, 540, 573, 600, 870.03, 870.11–870.14, 870.18, 870.28

[56] References Cited

U.S. PATENT DOCUMENTS

| | | | |
|---|---|---|---|
| 2,864,943 | 12/1958 | Schultz | 342/50 |
| 3,949,397 | 4/1976 | Wagner et al. | 342/45 |
| 4,042,906 | 8/1977 | Ezell | 340/870.13 X |
| 4,724,435 | 2/1988 | Moses et al. | 340/870.13 |

Primary Examiner—Bernarr E. Gregory
Attorney, Agent, or Firm—Beaton & Swanson

[57] ABSTRACT

A data entry and retrieval system utilizing a plurality of remote units in radio communication with a plurality of base units in electronic communication with a central processing computer. The base units establish links with transmitting remote units by the remote units choosing the base units with the best signal. The linked remote unit and base unit transmit using frequency hopping spread spectrum modulation, using a predetermined frequency hopping sequence and at a point in the sequence unique to the particular base unit. The system may be configured with a plurality of NODES, each of which has a unique predetermined frequency hopping sequence and assigned base units and remote units.

23 Claims, 4 Drawing Sheets

SPREAD SPECTRUM RADIO COMMUNICATION SYSTEM

This is a continuation-in-part of U.S. Ser. No. 343,602 filed Apr. 24, 1989, now abandoned, which is a divisional of U.S. Ser. No. 78,195 filed Jul. 24, 1987, now U.S. Pat. No. 4,835,372, which is a continuation-in-part of U.S. Ser. No. 862,278 filed May 12, 1986, now abandoned, which is a continuation-in-part of U.S. Ser. No. 757,277 filed Jul. 19, 1985, now abandoned.

BACKGROUND OF THE INVENTION

The present invention relates to a method and apparatus for operating a radio communication system for transmission of data among a multitude of base and remote units which employs a frequency hopping technique to minimize interference from external sources and among internal units.

The invention has particular, but not exclusive, utility in the health care environment. The invention allows for the identification of patients and patient-related items, and provides for quick and accurate updating of patient medical and accounting records.

Medical institutions are faced with a competitive environment in which they must improve profitability and yet simultaneously improve patient care. There are several factors which contribute to the ever increasing costs of hospital care. For example, there is an ever increasing amount of paperwork required by nurses, pharmacists and laboratory personnel. In addition, inaccurate recording of drugs, supplies and tests involved in patient care results in decreasing revenues by a failure to fully capture billing opportunities of these actual costs. Inadequate management also results in a failure to provide an accurate report of all costs involved in treating a particular illness. The lack of accurate and rapid transfer of patient information often reduces the accuracy or effectiveness of drug administration and patient care, thereby increasing the duration of hospital stay.

In addition, hospitals and other institutions must continuously strive to provide quality patient care. Medical errors, where the wrong patient receives the wrong drug at the wrong time, in the wrong dosage or even the wrong surgery, are a significant problem for all health care facilities. Many prescription drugs and injections are identified merely by slips of paper on which the patient's name and identification number have been handwritten by a nurse or technician who is to administer the treatment. For a variety of reasons, such as the transfer of patients to different beds and errors in marking the slips of paper, a patient may be given an incorrect treatment. Further, as health care facilities continue to decrease the number of staff personnel as a cost cutting measure, the possibility of personnel errors will most likely increase. Some of these problems have been addressed in U.S. Pat. No. 4,850,009 by Zook, assigned to the assignee of the present invention. The Zook patent describes a portable handheld terminal which includes a data-entry keyboard, a data-entry optical bar code reader and an RF transceiver. The bar code reader and the keyboard can be used to enter data regarding the patient identity, the type of drug to be administered or other information. The information is transmitted to a base transceiver which modulates the information and electronically communicates with a central recordation means such as a CPU. The base transceiver can transmit verifications or other limited information received from the CPU back to the portable handheld terminal. A set of terminals can also be in hard wire electronic communication with the CPU to enter and display data such as billing information. While the system described in the Zook patent is very effective, it is limited by the number of available non-interfering RF channels.

Some attempt has been made to overcome the inherent limitations of radio communications by utilizing spread spectrum technology. In spread spectrum systems, the radio signal is transmitted over a relatively broad band. This results in a lower power per bandwidth (W/Hz) but a broad channel. The low power at any given frequency within the channel lessens the potential for the system to interfere with other systems. At the same time, the broad channel allows a fairly large throughput rate.

The Federal Communications Commission ("FCC") has set aside certain radio frequency bands for low power communications devices using spread spectrum modulation. Current FCC regulations allow spread spectrum technology in the bands of 902-928 MHz, 2400-2483.5 MHz and 5725-5850 MHz. Because components are not readily available in the later two bands, most systems now in use are designed for operation in the 902-928 band. The FCC regulations require no site license but limit power to 1 watt. The most common spread spectrum systems employ direct sequencing methods, in which a signal is spread over a relatively broad band with the hope that frequency-specific interference will be overcome by clear transmissions elsewhere in the broad band. Direct sequencing methods have the advantage of relatively high throughput rates and low external interference problems. However, they use up a broad band, suffer from near-far problems and must have short range to keep under the FCC power limitations. The use of multiple channels can address the near-far problems, but at the cost of increased external interference problems, since each of the multiple channels is then a narrower band. When direct sequencing methods are used with multiple remote transceivers, it is generally necessary to utilize some form of carrier sensing multiple access ("CSMA") technique, in which each remote transceiver queues up to wait for an opening in the base transceiver. Therefore, while the overall transmission rate may be relatively high, the acknowledgement times may be unacceptably slow as the queued up remote units wait their turn for communication with the base transceiver.

Another spread spectrum technology is known as frequency hopping. In frequency hopping, the signal is in a relatively narrow channel as in conventional radio communication, but the channel hops among a predetermined set of frequencies within the spread spectrum. The FCC rules specify various permissible operating parameters for spread spectrum communications using the designated frequency bands such as the rate of frequency hopping and the frequency width and separation. As compared to direct sequencing, frequency hopping has the potential for longer range transmissions (since the limited power is not spread over a broad band) but presents some problems with fast synthesizers and synchronization requirements. Both systems tend to limit frequency specific external interference but in different ways; direct sequencing systems limit frequency specific external interference by spreading the signal over a wide band, while frequency hopping systems limit frequency specific external interference by hopping to a new, interference-free channel periodically. For purposes of the present invention, one of the most important differences is that dividing the spread spectrum into a large number of frequency hopping channels rather than a lesser number of direct sequencing channels results in fairly low throughput per channel but also results in a large number of non-interfering channels. Therefore, the overall throughput can still be high. Moreover, the acknowledgement times are very fast, because at any given time at least one of the large number of channels is likely to be available. This trade-off between throughput rates per channel and channel availability favors frequency hopping for applications with a large number of simultaneous transmissions of small information packets, and favors direct sequencing for applications with a small number of simultaneous transmissions of large information packets.

A frequency hopping technique is described in U.S. Pat. No. 4,850,036 by Smith for use with two-way communications links. Smith uses a fairly slow frequency hopping rate and is limited in its application by parameters that are optimized for two-way voice communication rather than data transmission. In particular, the transmission channel and reception channel are different in order to accommodate the two-way voice communication. Also, the Smith system contemplates remote units being locked to a given control unit without any capacity to choose the best signal from among physically separated control units.

SUMMARY OF THE INVENTION

The present invention provides an interactive computer link between a mainframe computer system and a large number of remote portable terminals, using RF spread spectrum frequency hopping. The operating parameters are deliberately optimized for transmitting small data packets requiring fast acknowledgement speeds. All the RF transmissions within an area of potential interference are on different channels, and the transmissions hop from channel to channel in a predetermined synchronous sequence, thereby precluding internal interference and minimizing external interference.

The system of the present invention includes a plurality of base transceivers and a plurality of remote transceivers within a NODE and may include a plurality of NODES. Within each NODE, the base transceivers and remote transceivers are synchronized and a predetermined frequency hopping sequence is utilized. Preferably, the predetermined frequency hopping sequence is unique among the NODES in a geographic area of potential interference, and each base transceiver within a NODE is at a unique point in the frequency hopping sequence, so that no two base transceivers in a NODE are on the same channel at the same time.

Each base transceiver transmits a calling signal on designated calling frequencies within the frequency hopping sequence. Each remote transceiver monitors the calling signals to establish a preferred base transceiver list. When the remote transceiver is in use, it draws from the preferred base transceiver list and transmits and receives at the point in the frequency hopping sequence corresponding to the point at which the base transceiver in the preferred list is transmitting, and then hops through the frequency hopping sequence with that base transceiver.

The system has very short acknowledgment times and a very fast frequency hopping sequence. The system is especially suited to transmitting and receiving small data packets.

DETAILED DESCRIPTION OF THE PREFERRED EMBODIMENT

Figure 1:
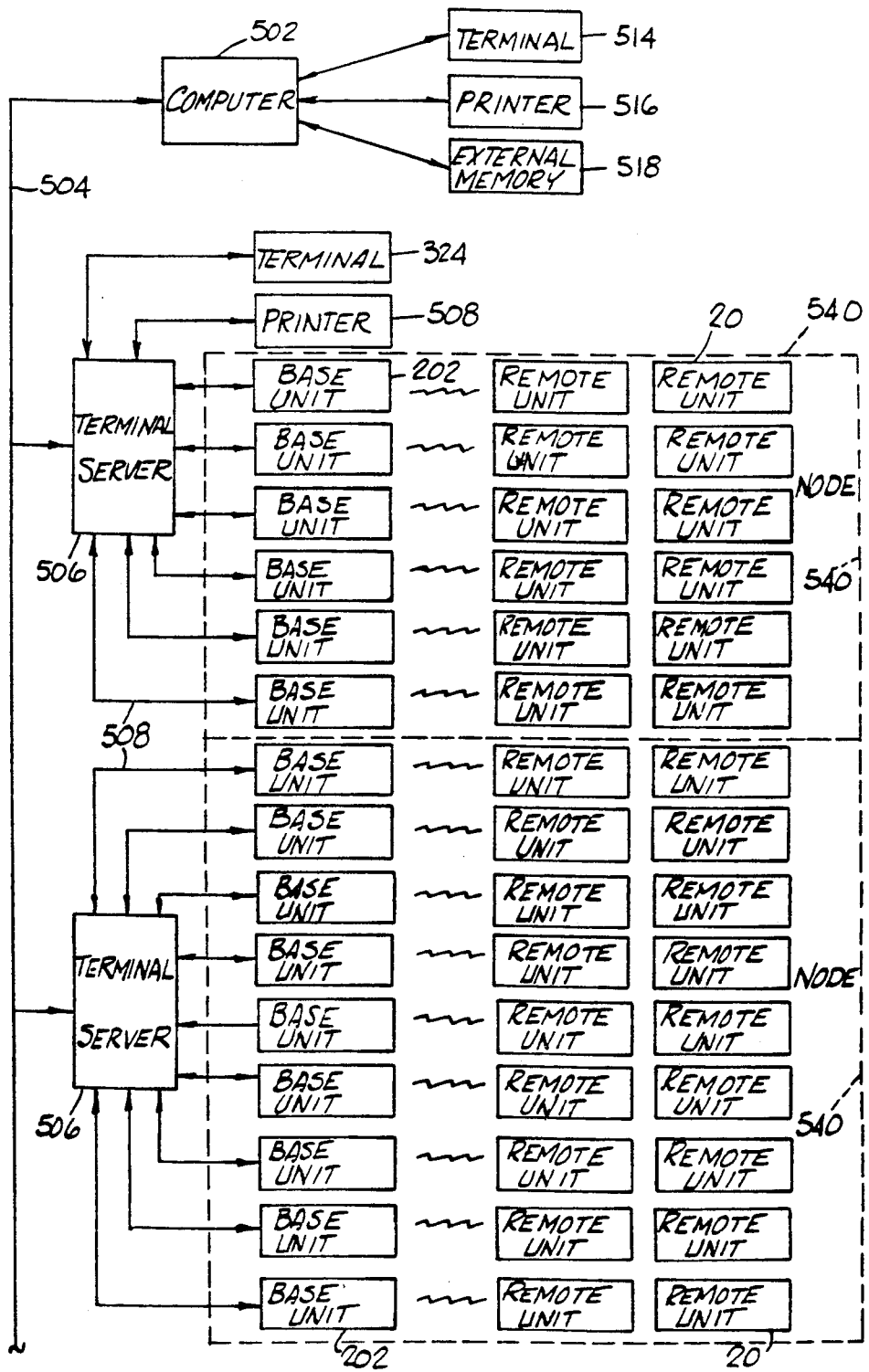
FIG. 1 is a representational diagram of the principal components of the system of the present invention.

The overall configuration the invention is shown representationally in FIG. 1. It consists of a network of remote units 20 and base units 202. A central processing computer 502 stores and processes a wide variety of information. The central processing computer 502 connects to a network such as an Ethernet 504 which connects to a set of terminal servers 506 located throughout the area to be served. A Xylogics model Annex II may be used as the terminal server. The terminal server holds the Ethernet software and is joined to a set of RS 232 communication lines 508 which are routed to the modems of the base units 202 as well as to computer terminals 324 that may be used to access the system. Printers 508 used to print information in the system may also be connected to the terminal server 506.

The computer system 502 may be directly connected to an access terminal 514, a printer 516 and an external memory 518 such as a magnetic tape or disk library.

The geographic areas of the locale to be served may be divided into NODES 540. Each NODE 540 contains its own set of base units 202 and remote units 20 and operates on its own frequency hopping sequence in the manner described below. Because in most applications the remote unit 20 is used intermittently, it is possible to include more remote units than base units in a given NODE. In a hospital environment where a remote handheld unit is in each patient room, for example, it may be feasible to limit the base units to one for each nursing station and to include several remote units for the same nursing station, depending on the particular operating demands.

Figure 2:
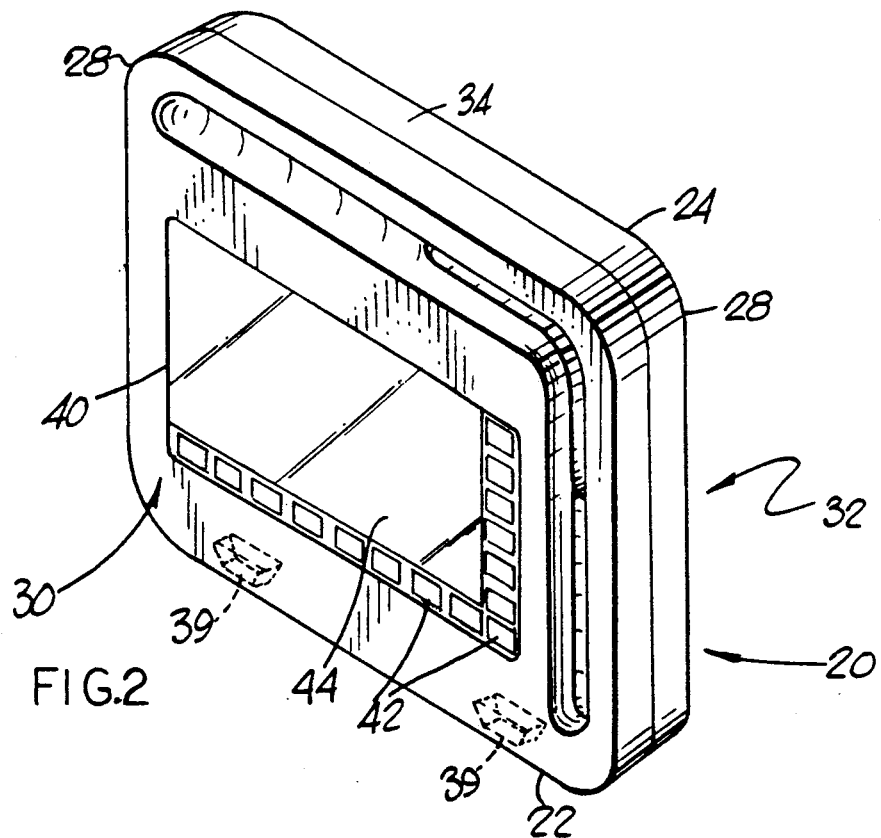
FIG. 2 is a perspective view of the remote unit of the present invention.

As shown in FIG. 2 the remote unit 20 of the invention includes a generally rectangular-shaped housing 22 having a handle portion 24. The handle portion 24 is an indented elongated region on the housing front and back and extending across the housing top and down one side. In the corner between the top and side, the indented handle portion 24 extends through the housing. The four corners 28 of the housing are rounded, and the intersections between the front 30 and back 32 surfaces with the side surfaces 34 are also rounded. This housing arrangement facilitates the grasping of the housing 24 in a variety of ways for carrying it, holding it and operating it. Of course, many other housing and handle arrangements are possible.

The housing 22 houses a touch screen 40 having a set of permanent command buttons 42 and a display portion 44. The touch screen may be a resistive analog type with separated mylar sheets over a glass screen. In the preferred embodiment, the touch screen has an eight bit controller that produces 256 by 256 resolution. The function and operation of the touch screen 40 is described below.

Figure 3:
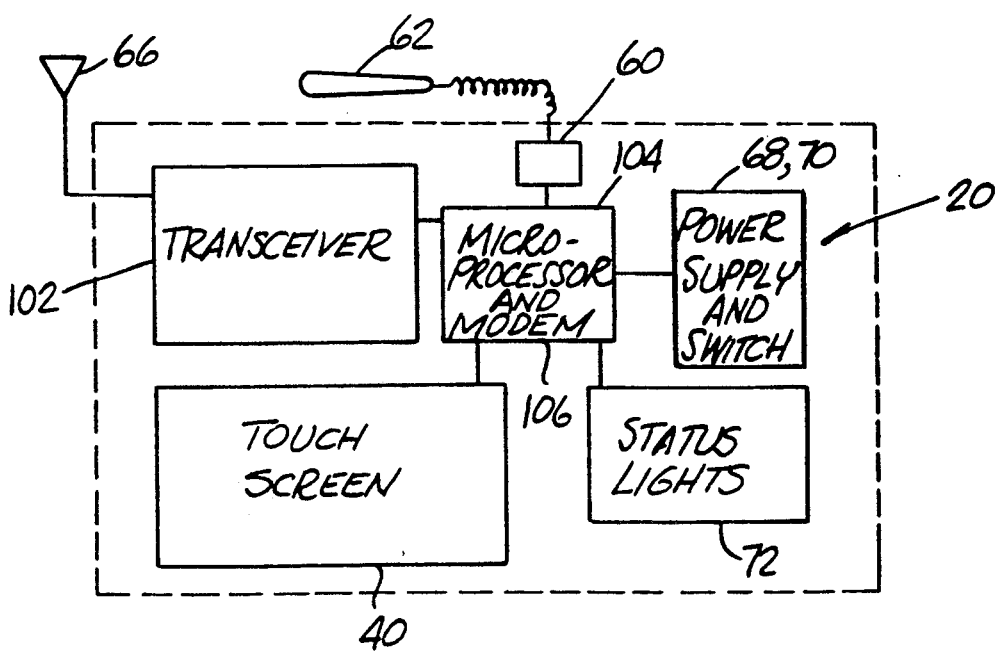
FIG. 3 is a representational diagram of the principal electronic elements of the remote unit of the invention.

The schematic diagram of FIG. 3 shows the basic electronic elements of the remote unit 20. Those elements include the touch screen 40 for entering and displaying data, the data entry port 60 which may receive an optical bar code reader 62 or other data entry device, an RF transceiver 102 which includes a transmitter and receiver, an RF antenna 66, a rechargeable power supply 68, switch means 70, microprocessor 104, modem 106, and status lights 72. The data entry port may accept the jack from an optical bar code reader such as a charged coupled device ("CCD") or optic RAM device or some other binary imaging device. Optical bar code readers are well-known in the art. Briefly, they include an optical lens and a low-powered, high sensitivity light source for illuminating bar code symbols. An image capture element includes an X-Y array of light sensitive pixels which digitize the bar code symbol. In operation, the user merely points the bar code reader at the symbols to be read and activates the bar code reader. The resulting "picture" obtained by the pixel array is digitized and electronically decoded by a microprocessor decoder that is integral with the reader. The bar code reader may include colored status lights or sound elements to indicate the power status, the fact that a bar code symbol has been successfully read, and other desired information. The bar code symbols may be Universal Product Code ("UPC") symbols, National Drug Code ("NDC") symbols, Health Industry Bar Code ("HIBC") symbols, Health Care Provider Application ("HCPA") symbols or other symbols.

The rechargeable power supply 68 is a conventional battery pack including a set of nickel cadmium or other rechargeable cells.

Figure 4:
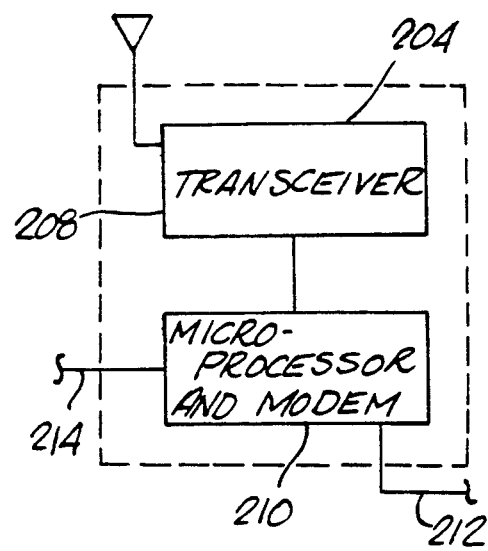
FIG. 4 is a representational diagram of the principal electronic components of the base unit of the invention.

The programmable microprocessor 104 may be an NEC V20 or other 8088 compatible device, preferably with 256K memory and capable of being populated to 640K. The microprocessor 104 synchronizes the RF transceiver 102 with the rest of the system and controls the modem 106. The base unit 202 is shown representationally in FIG. 4. The base unit 202 includes an RF transceiver 204, an antenna 206, a modem 208, a microprocessor 210, and a separate power supply 212 which may be ordinary AC. The base unit 202 interfaces via the modem 208 with an RS 232 communications line 214 which, in turn, is interconnected with a central computer through a terminal server and an Ethernet in the manner described below.

Figure 5:
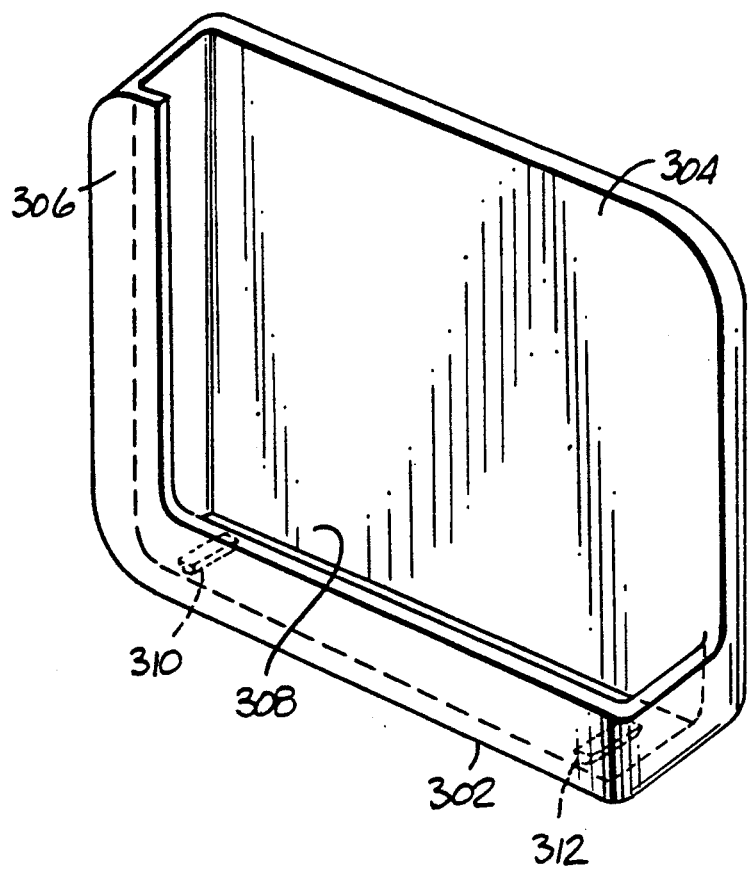
FIG. 5 is a perspective view of the remote unit engage with the recharging unit of the invention.

The remote unit 20 is stored and recharged in a recharging unit 302 shown in FIG. 5. The recharging unit 302 includes a back portion 304 and a front portion 306 spaced apart to form a cradle area 308 to receive and hold the remote unit 20. A pair of contact terminals 310 and 312 in the bottom of the cradle area 308 contact and establish electrical communication with mating spring terminals 37 and 39 which are electrically connected to the rechargeable power supply 68 in the remote unit 20. The recharging unit is connected to an ordinary AC power supply and includes a transformer to convert to appropriate recharging current. The recharging unit 302 may include attachment means such as hooks or screw holes for fastening it to a wall or other desired location.

Each base unit transceiver 204 is configured as a MASTER and each remote unit transceiver 102 is configured as a SLAVE. Each base unit transceiver 204 has an address which includes the address of its NODE and an individual address to identify the particular transceiver within the NODE. The separate transceiver address for each transceiver within a NODE is unique within that NODE. One of the base unit transceivers 204 within each NODE is configured as a NODE MASTER. In this manner, the base unit transceivers 204 have a NODE address and individual addresses, such as 0 for the NODE MASTER and 1, 2, 3, etc. for the others. The NODE addresses within the overall system may not be unique, so long as NODES with the same address are not within interference range of one another.

The total band width used by the system is divided into 64 channels plus 16 calling channels. Within a NODE, each of the up to 64 base unit transceivers 204 will begin on a different channel, and all will follow the same frequency hopping sequence. Therefore, no two base unit transceivers are on the same channel at the same time. The frequency hopping sequence generally follows a pattern of three data channels, a calling channel, three data channels, a calling channel, and so on.

Each SLAVE continually monitors all the calling channels to detect calling transmissions by the MASTERS within the NODE. The SLAVES maintain a list of the best MASTER signals (the best eight in the preferred embodiment), which is updated each time the SLAVE receives another MASTER transmission on a calling channel. The quality of the MASTER signal can be measured preferably by error rates or alternatively by signal strength. When the portable handheld terminal is operated, it transmits to and receives from the best available MASTER, based on the periodically updated preferred list it maintains.

The list of the preferred MASTERS includes the address of each MASTER which was contained in the calling transmission and also the stage of each of those MASTERS in the frequency hopping sequence. The later is determined by noting the calling frequency of each MASTER at the time its address was entered in the preferred MASTER list, and then advancing the channel through the frequency hopping sequence at each frequency hopping interval. Thus, the SLAVE can link to the best available MASTER at any given time and can determine the stage of the MASTER in the frequency hopping sequence. The SLAVE then can immediately begin transmitting to that particular MASTER by transmitting on its channel which is unique within the NODE. The SLAVE and MASTER utilize the same frequency hopping sequence, so they hop together to the next channel in that sequence at the next frequency hopping interval.

During the time that a SLAVE and MASTER are linked, the SLAVE continues to monitor the calling frequencies in order to update its preferred MASTER list. If that updating process indicates that another MASTER is better received than the MASTER to which is currently linked, then at the time the SLAVE commences its next communication linkage it will link to that other MASTER and will track its frequency hopping. Alternatively, the SLAVE can be programmed to change channels to the new MASTER at the next frequency hopping rather than waiting until the next communication linkage.

Figure 6:
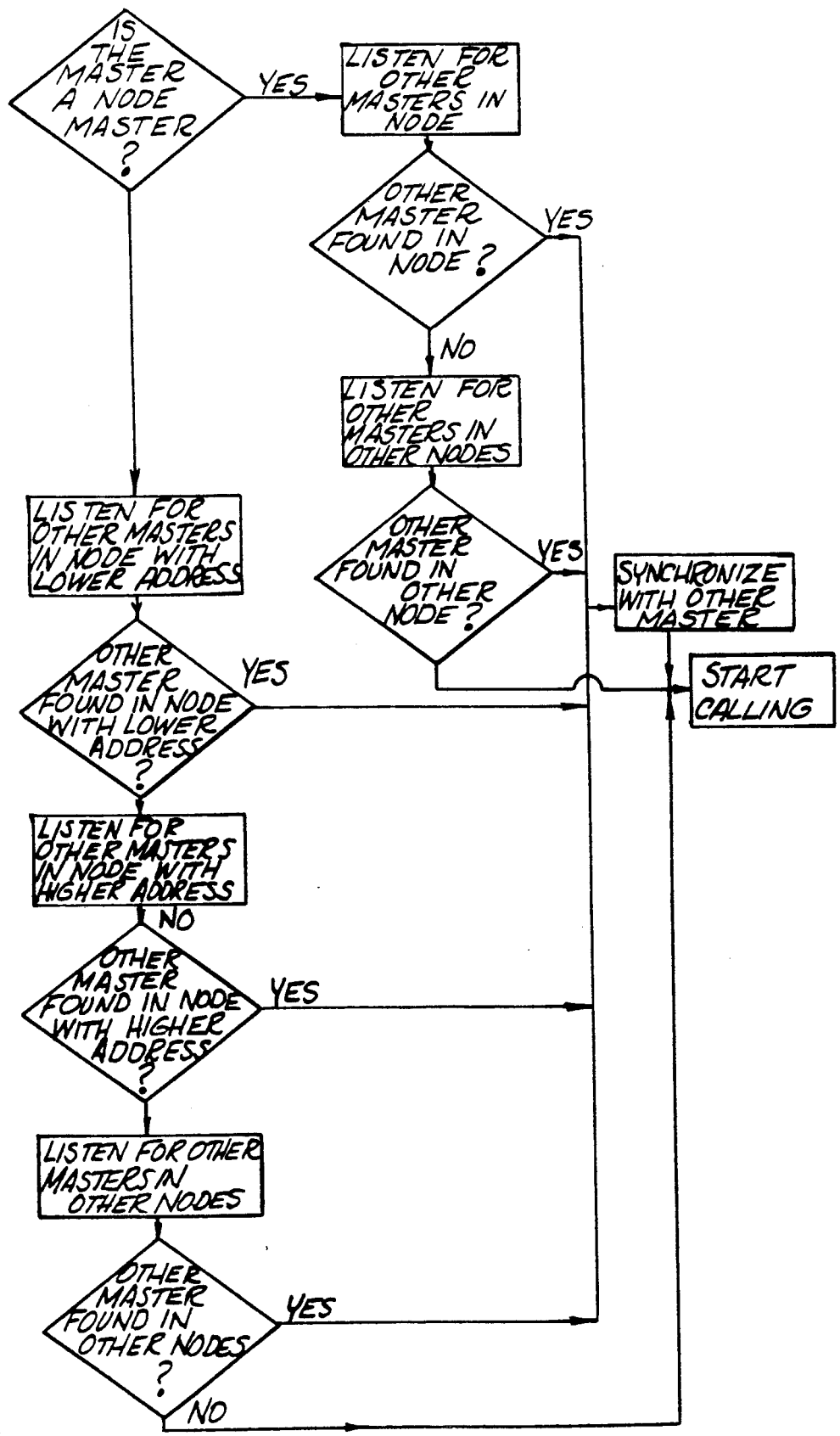
FIG. 6 is a flow chart diagram of the synchronization procedure of the invention.

On start-up of the system, the base unit transceivers 204 and remote unit transceivers 20 will all synchronize. This is accomplished in accordance with the flow chart of FIG. 6. The procedure differs depending on whether the MASTER is a NODE MASTER. If it is a NODE MASTER, it first listens on the calling frequencies for other MASTERS within its NODE. If it detects one, it synchronizes to it and then begins transmitting on the calling frequencies to indicate its availability. If it does not detect other MASTERS within its NODE within a predetermined length of time (such as one second), it listens for other MASTERS in other NODES If it detects one, it synchronizes to it and then begins transmitting on the calling frequencies. If it does not detect other MASTERS in other NODES within a predetermined time, it simply begins transmitting on the calling frequencies without being previously synchronized.

If the MASTER is not a NODE MASTER, then it first listens for other MASTERS in its NODE with a lower address. If it detects one, it synchronizes to it and then begins transmitting on the calling frequencies to indicate its availability. If it does not detect a MASTER with a lower address after a predetermined time, it listens for other MASTERS in its NODE with higher addresses. The predetermined time varies among each MASTER in relation to its address, so that MASTERS with higher addresses listen for longer predetermined times. If the MASTER detects a MASTER in its NODE with a higher address, it synchronizes to that MASTER and begins transmitting on the calling frequencies. If it does not detect a MASTER in its NODE with a higher address, it listens for MASTERS in other NODES. If it detects one, it synchronizes to it and begins transmitting on the calling frequencies. If it does not detect one, it simply begins transmitting on the calling frequencies without being previously synchronized.

It can be seen that this synchronization procedure will cause the base unit transceivers 204 in the various NODES to be synchronized with one another by establishing a reference of the transmitting transceiver with the lowest address. If a MASTER is turned off for any reason, it will re-synchronize to the reference upon start-up. A typical transmission packet from a base unit transceiver 204 to a remote unit transceiver 102 begins with a synchronization byte, a NODE address and a base transceiver unit address identifying the remote unit transceiver to which the base unit transceiver 102 is transmitting. After that is a portion to establish the format of the packet (such as a data packet, a calling packet or a synchronization packet), an identification number portion to identify the packet, a data counter to specify the number of data bytes in the packet in the case of a data packet, an error detection byte, a set of data up to 127 bytes in the case of a data packet, and a 4 byte error detection data. The error detection is by known cyclic redundancy checks. If there is an error, the base transceiver unit so indicates by failing to send an acknowledgment upon receiving the packet.

Each time period between frequency hopping (that is, each time period during which a MASTER or SLAVE is on a given frequency) is referred to as a time slot. Each time slot may be divided into time subslots in the manner described below.

After a MASTER has been synchronized with other MASTERS in accordance with the procedure described above, it enters a calling mode wherein it transmits a calling token over the calling frequencies. A calling frequency slot is divided into five subslots. During the first subslot, the MASTER transmits a token packet containing its address. The calling token packet number will be identified as the next noncalling frequency in the MASTER'S frequency hopping sequence, so that any responding SLAVE will know where to jump to link up with the MASTER. During the next subslot the MASTER will listen for any responding SLAVES, and during the last three subslots the MASTER will listen for any other MASTERS on all calling frequencies. If the MASTER detects a responding SLAVE, it will enter a connect mode as described below. If the MASTER detects other MASTERS, it will synchronize to any such MASTERS with a lower address, and then transmit the new synchronization to any responding SLAVE.

If the MASTER transmitting a calling token on a calling frequency detects a responding SLAVE during the SLAVE response subslot, the MASTER enters a connect mode beginning with the next time slot. The MASTER shifts to the noncalling frequency sequence and chooses the appropriate stage in that sequence in accordance with its address. The responding SLAVE shifts to the noncalling frequency sequence along with the MASTER.

The first subslot transmission by the MASTER on the noncalling frequency is a token packet identified with a packet number. The SLAVE subslot response has the same identifying packet number. Upon detecting the SLAVE response with the same packet identifying number, the MASTER will increment the next packet as an indication that the preceding packet was transmitted and received. Any data received by the MASTER from the SLAVE is duly modulated and communicated with the central processing unit over the Ethernet. Any data from the central processing unit and acknowledgments are transmitted by the MASTER to the SLAVE.

During any subslots when there is nothing to transmit or receive, the MASTER will listen to the calling frequencies. If it detects any MASTERS with lower addresses, it will synchronize to them and then transmit the new synchronization to the SLAVE. Also, the MASTER will transmit a calling token every four time slots on the calling frequencies. This is to allow other SLAVES to monitor their reception of that MASTER, but the calling token contains an indication that the MASTER is currently linked with a SLAVE so that other SLAVES do not attempt to transmit to it.

If the MASTER does not detect a SLAVE response to the MASTER'S last transmission within a predetermined period (64 slots in the preferred embodiment), the MASTER will assume that the SLAVE is no longer being used or that reception has degraded, and the MASTER will return to the calling mode. Also, the MASTER will assume that it has lost synchronization and will return to the synchronization procedure if it does not detect another MASTER on the calling frequencies for 30 seconds. Otherwise, the MASTER will remain linked with the SLAVE in the connect mode until it receives a disconnect signal from the SLAVE, at which time it will return to the calling mode.

As an alternative to the process whereby each SLAVE maintains and updates a preferred list of MASTERS, each SLAVE can instead simply be permanently linked with a MASTER. This alternative may not result in the best possible transmission between MASTERS and SLAVES, although the transmission is likely to be relatively good if some thought is given beforehand to the physical proximity of the two transceivers and the location and character of the potential interference. Another drawback to such fixed linking is that it essentially prevents the NODE from utilizing a number of greater than the number of base units, because this would result in several SLAVES linked with each MASTERS. If one of these SLAVES was in communication with the linked MASTERS, then the others would have to wait for an opening. In the preferred list procedure, this problem is avoided by the others simply choosing the next best MASTER from the preferred list.

The frequency hopping is preferably at 25 millisecond intervals and is accomplished in 150 microseconds or less. This fast hopping rate is especially useful in transmitting relatively small packets of information and receiving very fast acknowledgements. It also limits channel-specific interference to the 25 millisecond duration of a single channel.

The frequency hopping sequence may be predetermined randomly or predetermined with some consideration to interference phenomena. If the frequency hopping sequence is predetermined with some consideration to interference phenomena, this consideration may involve known multipathing and fading patterns.

The modems are synthesized 130 channel FM transceivers with a 200 kHz channel band width. They utilize a 76 kBand data rate with a synchronous format and packet sizes of 128 data bytes. The RF power is 50 mW nominal, and the modulation is standard FSK with 50 kHz deviation. A duobinary precoding is used which lowers the sideband energy and removes the DC component in the data. In the preferred embodiment, the receiver portion is dual conversion with a −60 dBimage response and −102 dbm sensitivity.

The system may be used in a variety of settings. As indicated at the outset, the system has particular but not exclusive utility in the health care environment as a patient data entry and retrieval device. In that application, the central computer is programmed to store and process patient-related data such as patient medical information (vital signs, allergies, medication regiment, etc.) and other patient-related information (usage of disposables, prescription information, accounting information, etc.). Such information particularly lends itself to being entered, processed, stored and retrieved by this system, because fast acknowledgement times are necessary, small packets of information are transmitted, and a large number of access terminals are necessary.

The particular software for use of the system in a health care environment will vary depending on the needs and preferences of the users. An example of such software from a user's perspective for use in a similar system is in U.S. Pat. No. 4,850,009 by Zook, et al., issued Jul. 18, 1989 and assigned to the assignee of the present patent, the contents of which are hereby incorporated by reference. Briefly, a user such as a nurse can access the system through a remote unit only by entering a personal identification code, either by reading a user's bar coded badge with the bar code reader or by entering an alpha-numeric code through the keyboard. The use of the system can then be largely by menus and submenus. If desired, the system can be programmed to limit access depending on the user status (medical professionals may have access not available to clerical workers, for example) or by physical area (persons in one department might not be able to access records generated in another department) or by any other category desired by the users and programmed into the system.

What is claimed is:

1. A method for radio communication of data using a central processing computer, a set of base units, with transceivers, in electronic communication with said central processing computer, and a set of remote units, with transceivers, in RF communication with said base transceivers, all of said transceivers having limited transmission range, comprising:
    (a) establishing a set of nodes and node containing at least one base unit and at least one remote unit;
    (b) establishing a plurality of radio frequency channels for transmission of radio signals between the base unit transceivers and the remote unit transceivers;
    (c) establishing and assigning to each said nodes a channel hopping sequence from said plurality of frequency channels, whereby no two said sequences assigned to nodes with transceivers within transmission range of one another are the same;
    (d) transmitting calling signals from the base unit transceivers to the remote unit transceivers;
    (e) receiving said calling signals with said remote unit transceivers, monitoring the quality of the received signals with said remote unit, and establishing in the remote unit a preferred list of base units based upon the quality of the received signals;
    (f) linking a transmitting remote unit with a base unit drawn from said preferred list of base units; and
    (g) transmitting data between said remote unit and said central processing computer utilizing said linked transmitting remote unit and base unit.

2. The method of claim 1, wherein said step of monitoring the quality of the received signal with said remote unit is accomplished by measuring error rates.

3. The method of claim 2, wherein said step of measuring error rates is by a cyclic redundancy check.

4. The method of claim 1, wherein said calling signals include an identification of the calling base unit transceiver and wherein said calling transmissions are on dedicated calling frequency channels drawn from said plurality of frequency channels.

5. The method of claim 4, wherein said linking step includes:
    (a) transmitting from a remote unit transceiver to said base unit transceiver transmitting calling signals, a remote unit linking response; and
    (b) transmitting and receiving between said base unit transceiver and said remote unit transceiver on a noncalling frequency channel in said channel hopping sequence.

6. The method of claim 5, wherein said linking step further includes both of said linked remote unit transceiver and base unit transceiver hopping through said assigned channel hopping sequence in unison.

7. The method of claim 6, wherein said base unit transceiver continues periodically transmitting calling signals on said calling frequency channels while linked with said linked remote unit, said calling signals containing an indication that the base unit is linked to a remote unit.

8. The method of claim 8, wherein transmissions by said linked base unit to said linked remote unit are in packets, each packet containing a packet number, the packet number being incremented each time the base unit receives response from the remote unit.

9. The method of claim 6, wherein said linked base unit is unlinked from said linked remote unit if no remote unit response to the linked base unit transmission is received on the noncalling frequency channel within a predetermined time.

10. The method of claim 6, wherein said set of remote units is a plurality of remote units.

11. The method of claim 10, wherein said set of base units is a plurality of base units.

12. The method of claim 11, wherein said set of nodes is a plurality of nodes.

13. The method of claim 12, wherein the base units are synchronized.

14. The method of claim 13, wherein said synchronization is accomplished by:
   (a) each base unit, upon loss of synchronization, detecting another base unit transmitting on the calling frequencies within said nonsynchronized base unit's node; and
   (b) synchronizing to said another base unit.

15. The method of claim 14, wherein said plurality of base units have a series of identifying addresses, so that each said base unit has a unique address from said series, wherein said step of synchronizing to said another base unit includes preferentially synchronizing to the synchronized base unit with an address toward one end of said series in the event that the nonsynchronized base unit detects more than one synchronized base units transmitting on the calling frequencies.

16. The method of claim 15, wherein said synchronization includes the nonsynchronized base unit transmitting without being synchronized in the event said nonsynchronized base unit does not detect a synchronized base unit transmitting on the calling frequencies.

17. A system for radio frequency communication of data, comprising:
   (a) a central processing computer;
   (b) a plurality of base units, with transceivers in electronic communication with said central processing computer;
   (c) a plurality of remote units, with transceiver, for radio data communication with said base units, whereby each data communicating remote unit is linked with a base unit;
   (d) means for hopping each said linked remote unit and base unit through a predetermined sequence of a plurality of radio data frequency channels;
the plurality of base units and plurality of remote units being grouped into a plurality of nodes, all of the transceivers in each node having a single predetermined channel sequence that is different from the predetermined channel sequence of transceivers in other nodes within the transceiver range.

18. The system of claim 17, wherein the base units in each node are on different frequency channels as they hop through said predetermined channel sequence, whereby no two base units in a single node are on the same frequency channel at the same time.

19. The system of claim 18, wherein said remote units are battery operated.

20. The system of claim 19, wherein said remote units include means for displaying data received from the central processing computer.

21. The system of claim 20, wherein said remote units include means for entering data for transmission to the central processing computer.

22. The system of claim 21, wherein said display means and entering means is a touch screen.

23. The system of claim 19, further comprising recharging units for recharging the remote unit batteries.

* * * * *